US012629490B2

(12) United States Patent
Himmelstoss et al.

(10) Patent No.: US 12,629,490 B2
(45) Date of Patent: May 19, 2026

(54) VENTILATOR COMPRISING OPERATING DEVICE HAVING HAPTIC FEEDBACK

(71) Applicant: Hamilton Medical AG, Bonaduz (CH)

(72) Inventors: Matthias Himmelstoss, Chur (CH); Urs Lendenmann, Chur (CH)

(73) Assignee: HAMILTON MEDICAL AG, Bonaduz (CH)

( * ) Notice: Subject to any disclaimer, the term of this patent is extended or adjusted under 35 U.S.C. 154(b) by 1418 days.

(21) Appl. No.: 16/649,401

(22) PCT Filed: Sep. 13, 2018

(86) PCT No.: PCT/EP2018/074791
§ 371 (c)(1),
(2) Date: Dec. 15, 2020

(87) PCT Pub. No.: WO2019/057606
PCT Pub. Date: Mar. 28, 2019

(65) Prior Publication Data
US 2021/0128853 A1 May 6, 2021

(30) Foreign Application Priority Data
Sep. 22, 2017 (DE) ..................... 10 2017 122 046.1

(51) Int. Cl.
*A61M 16/00* (2006.01)

(52) U.S. Cl.
CPC ...... *A61M 16/024* (2017.08); *A61M 16/0003* (2014.02); *A61M 2016/0015* (2013.01); *A61M 2016/0039* (2013.01); *A61M 2016/0042* (2013.01); *A61M 2205/502* (2013.01); *A61M 2205/582* (2013.01); *A61M 2230/205* (2013.01)

(58) Field of Classification Search
CPC ........... A61M 16/024; A61M 16/0003; A61M 2016/0015; A61M 2016/0039; A61M 2016/0042; A61M 2205/502; A61M 2205/582; A61M 2230/205; A61M 16/04; A61M 16/00; G06F 3/016; G06F 3/0362; G06F 3/04847
See application file for complete search history.

(56) References Cited

U.S. PATENT DOCUMENTS

| | | | | |
|---|---|---|---|---|
| 9,063,570 B2 * | 6/2015 | Weddle | .................. | G06F 3/016 |
| 2010/0095961 A1 * | 4/2010 | Tornesel | ........... | A61M 16/0051 128/205.24 |
| 2012/0268285 A1 * | 10/2012 | Hansen | ................... | G06F 3/016 340/691.1 |
| 2017/0209664 A1 * | 7/2017 | Potharaju | ........... | A61M 16/109 |

* cited by examiner

*Primary Examiner* — Timothy A Stanis
*Assistant Examiner* — Matthew R Moon
(74) *Attorney, Agent, or Firm* — Wiggin and Dana LLP

(57) ABSTRACT

A ventilation device for mechanically ventilating patients includes an operating device for setting at least one ventilation parameter. The operating device includes a manipulation element that can be manually operated by an operator to manually set the at least one ventilation parameter, and a control unit operable to automatically determine a target value for the at least one ventilation parameter on the basis of detected values of characteristic variables. The operating device is provided with a first haptic feedback unit configured to control the manipulation element in terms of a first haptic feedback to provide perceptible feedback, emphasizing the position of the manipulation element corresponding to the target value determined by the control unit.

15 Claims, 4 Drawing Sheets

Second haptic feedback

First haptic feedback

Second haptic feedback

First haptic feedback

VENTILATOR COMPRISING OPERATING DEVICE HAVING HAPTIC FEEDBACK

Figure 1:
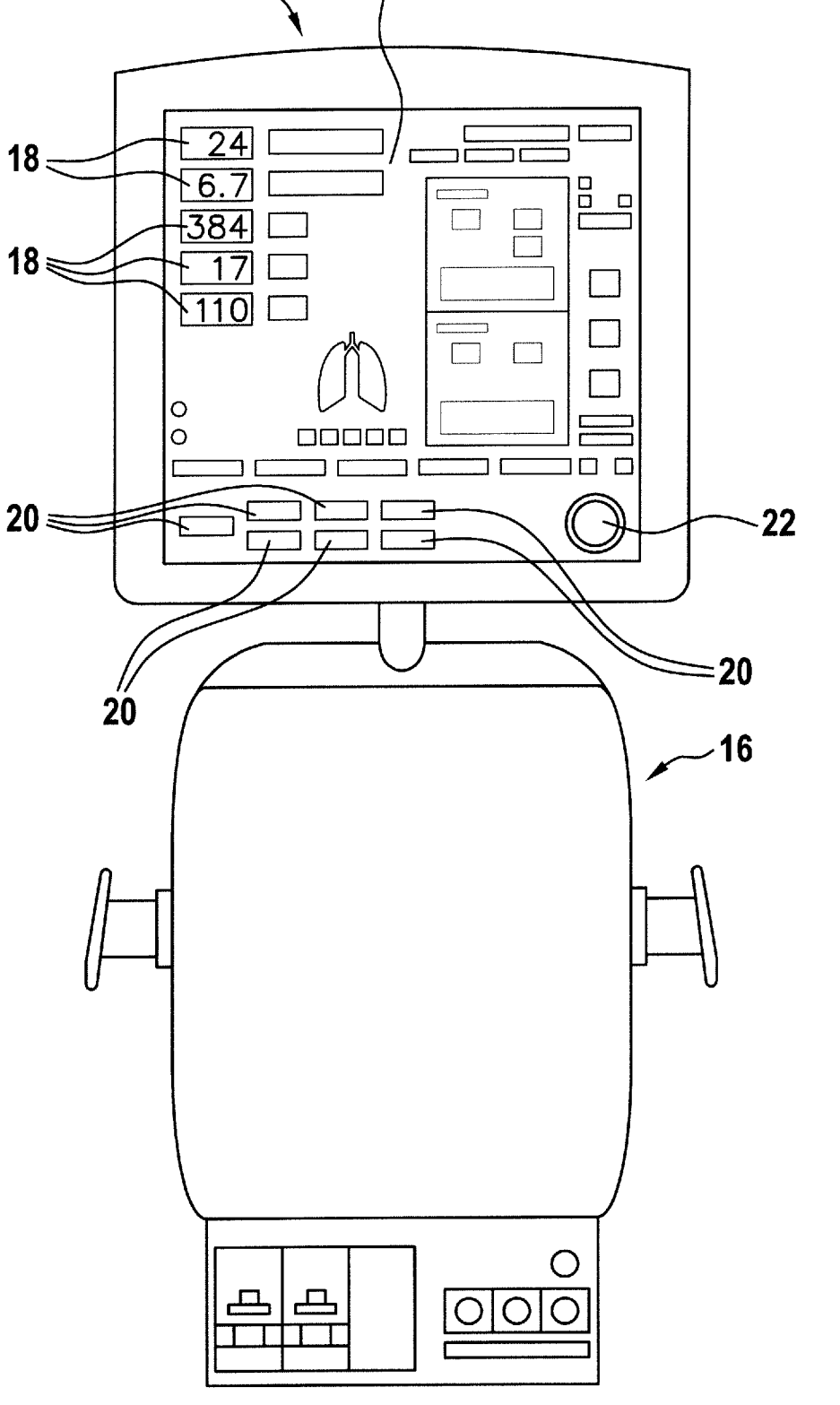

The present invention relates to a ventilation device for mechanical ventilation of patients, comprising an operating device for setting at least one ventilation parameter, having a manipulation element which can be manually operated by an operator for manually setting the at least one ventilation parameter. The present invention also relates to a method for providing a supportive interaction in setting at least one parameter of a ventilation device as well as to a computer program product which contains program instructions, the execution of which on a data processing system implements a corresponding method for providing a supportive interaction in setting at least one parameter of a ventilation device.

In particular, the ventilation device is to be provided with a control unit which is designed to automatically determine a target value for the at least one ventilation parameter on the basis of detected values of characteristic variables.

It is suggested that the operating device has a first haptic feedback unit associated therewith which is designed to control the manipulation element in terms of a first haptic feedback such that a position of the manipulation element corresponding to the target value of the at least one ventilation parameter determined by the control unit is highlighted or emphasized so as to be perceptible for the operator.

In addition, or as an alternative to this, the operating device can have a first haptic feedback unit associated therewith which is designed to generate a first haptic feedback that is determined on the basis of a deviation between the value of the ventilation parameter currently set by manual operation of the manipulation element and the target value of the ventilation parameter determined by the control unit. The term deviation is to be understood in general to mean any kind of deviation of the currently set value of the ventilation parameter from the target or desired value. Such a deviation can be detected, for example, as a difference, a ratio or a different relationship between the currently set value and the target value.

Up to now, the setting of ventilation parameters in ventilation devices as a rule has been effected such that one or more ventilation parameters are set manually by manipulating a manipulation element, for example a rotary knob, according to a specific treatment situation of a patient, or are reset or adjusted according to a change in the patient's situation. This procedure often requires several adjustment steps, as in most cases a change in one of the ventilation parameters takes effect on other ventilation parameters and thus necessitates a further adjustment of such other ventilation parameters. The adaptation of these other ventilation parameters then usually has an effect on the ventilation parameter that was changed first, so that it must be readjusted, etc. This procedure is tedious and requires a lot of experience. Even with a lot of experience, the correct readjustment of all ventilation parameters according to a patient's condition or when the patient's condition changes is time-consuming. Attempts to automate the previous manual setting procedures have largely remained unsuccessful, in particular because automatic procedures for setting or readjusting ventilation parameters by the ventilation device are often confronted with little acceptance by the operating staff in intensive care units and hospitals. Treating doctors or intensive care staff generally want to keep control over a patient's ventilation status and are therefore very reluctant to introduce automated procedures for ventilation devices.

For example, WO 2008/113410 A1 shows a manipulation element for manually setting a ventilation parameter, in particular the opening pressure of a pressure limiting valve in a ventilation device. The manipulation element is acted upon haptically during the adjustment so that reaching of a limit value of the ventilation parameter becomes perceptible. The limit value for the ventilation parameter is fixedly determined and the haptic feedback for the manipulation element is generated on the basis of the degree of adjustment of the manipulation element from an initial position.

U.S. Pat. No. 6,834,647 B2, on the other hand, shows a manually operated remote control for a ventilation device, by means of which manual ventilation by a doctor can be carried out, which simulates ventilation by means of an Ambu bag. In particular, a haptic feedback is to be generated in the remote control on the basis of a measured ventilation parameter, in particular the airway pressure, which gives the doctor a tangible feedback about the currently prevailing value of the ventilation parameter, corresponding to the feedback during manual ventilation using an Ambu bag.

The invention meets the underlying object of simplifying the manual setting of a ventilation parameter by an operator.

For meeting this object, there is suggested a a ventilation device for mechanical ventilation of patients, comprising an operating device for setting at least one ventilation parameter, having a manipulation element that can be manually operated by an operator for manually setting the at least one ventilation parameter, and a control unit which is designed to automatically determine a target value for the at least one ventilation parameter on the basis of detected values of characteristic variables, wherein the operating device has a first haptic feedback unit associated therewith which is designed to control the manipulation element in terms of a first haptic feedback such that a position of the manipulation element corresponding to the target value of the at least one ventilation parameter determined by the control unit is emphasized so as to be perceptible for the operator.

In particular, the control unit can be designed such that it performs or works through at least one automated operating control/regulation procedure for the fully automatic ventilation of patients, as a rule on the basis of a specific ventilation model. Examples of such partially or almost completely automated ventilation procedures are known, for example, under the designations "ASV" and "INTEL-LIVENT-ASV" in the applicant's ventilation devices. The automatic ventilation procedure works in a so to speak invisible way or "in the background". This is intended to express that one or more of the ventilation parameters determined by the ventilation procedure are not applied directly by the ventilation device for ventilation. Rather, these ventilation parameters should still be settable only manually by manual operation of the manipulation element by an operator. Nevertheless, the automatically calculated ventilation parameters, even if they are not to be used directly for automatic ventilation, should be taken into account during ventilation, in terms of a haptic feedback that retroacts on the manipulation element in the course of the manual setting.

The solution proposed here makes it possible to provide intuitive support by the ventilation device in the case of manual manipulation of the manipulation element, without thereby impairing the control options for the operator. The solution suggested here develops the state of the art with regard to the intuitive operability of a ventilation device, but still allows all possible manual control options that may be desired for an operator. In particular, the solution suggested here implies haptic feedback on the basis of a ventilation parameter specified or determined by the ventilation device, or on the basis of a model of the patient's condition applied by the ventilation device and/or the ventilation strategy to be used in each particular case or the ventilation mode to be selected in each particular case, from which the respective optimum ventilation parameters can be derived for the respective patients condition. This supports the operating staff in taking into account sometimes very complex relationships between individual ventilation parameters when manually setting or changing a ventilation parameter. It is important in this regard that the solution proposed here improves the perceptibility of such relationships, in a very intuitive way. In particular, the solution suggested here makes it possible to sense such relationships, in particular immediately in response to manual manipulation of the manipulation element for the purpose of resetting or readjusting one of the ventilation parameters. Such complex relationships may be, for example, pressure-volume relationships as they are recommended for the respective settings of basic parameters that are intended to reflect the patient's condition. This help in setting ventilation parameters ultimately increases the safety in mechanical ventilation because the operating staff is warned against effecting unusual settings of ventilation parameters or in any case settings not corresponding to common ventilation parameters.

The term target value is to be understood to include both a single value and a certain range of values or a value limit, such as an upper limit or a lower limit. The expression "emphasized so as to be perceptible" is intended to express that the operator experiences a feedback generated by the ventilation device in the course of a manipulation process of the manipulation element, which feedback can be recognized by any sensory perception. In particular, the feedback can be felt, that is to say, upon contact with the ventilation device, in particular upon contact with the manipulation element, it can trigger a tangible sensory perception. This type of feedback is generally referred to as haptic feedback. In particular, the haptic feedback should be detectable with the same organ that acts on the manipulation element for setting the operating parameter. For example, in the case of a manual setting of the ventilation parameter using a hand of the user, haptic feedback can act on the hand, or in any case an organ associated with the hand, in particular on one or more fingers or the palm of the hand. The haptic feedback can act, for example, in the form of a resistance which the manipulation element opposes to further adjustment in the direction applied by the operator. The resistance that the manipulation element opposes to manipulation of the manipulation element may decrease the more a manipulation of the manipulation element is directed towards a value of the respective ventilation parameter to be set that is preferred by the control unit of the ventilation device. The decrease can also take place suddenly or abruptly, in order to give the operator a "latching" feeling when a position is reached in the course of a manipulation process which corresponds to a value of the ventilation parameter proposed by the control unit of the ventilation device. Conversely, the resistance that the manipulation element opposes to manipulation of the manipulation element may increase the more a manipulation of the manipulation element is directed away from a value of the respective ventilation parameter to be set that is preferred by the control unit of the ventilation device. Here too, after a value of the ventilation parameter proposed by the control unit of the ventilation device is exceeded, the resistance can be increased suddenly or abruptly when the manipulation element is further operated manually.

The haptic feedback unit in particular may comprise a drive for generating a haptic feedback, and a sensor system for detecting or recording one or more parameters on the basis of which the haptic feedback is set. For this purpose, the haptic feedback unit can have a control/regulating unit that is configured with suitable control algorithms. The drive can be designed to generate a suitable haptic feedback, for example in the form of a feedback force, a feedback moment, and/or a tangible feedback movement. The effects mentioned can be established individually, but in many cases it will be beneficial to superimpose at least two of these effects. A haptic feedback force or a haptic feedback moment can, for example, cause a change in a resistance counteracting an adjustment of the manipulation element when the manipulation element is adjusted in increasing or decreasing direction. A haptic feedback movement can take the form of an adjustment-dependent tangible movement of the manipulation element, in particular the form of a vibration when the manipulation element reaches or is near a target or desired position. For example, a servo drive with suitable control of position, speed and/or torque on the basis of predetermined input parameters is suitable as drive for the haptic feedback unit. For example, electronically controlled servo drives meet high to very high dynamic requirements and are able to generate a suitable haptic feedback acting on the manipulation element immediately in response to detection of one or more ventilation parameters and/or detection of a change in the position of the manipulation element. Suitable sensors for detecting the one or more ventilation parameters and/or for detecting the position or an adjustment of the manipulation element from an initial position will be present in many cases anyway and can readily be utilized for generating the haptic feedback. Merely by way of example, reference may be made to sensors for detecting pressure and/or gas flow in airway lines from the ventilation device to the patient and/or away from the patient, or sensors for detecting oxygen saturation in arterial blood by means of pulse oximetry or other methods. Sensor systems for detecting a current position of the manipulation element or for detecting an adjustment of the manipulation element from an initial position can be implemented, for example, on the basis of electric and/or magnetic fields that are created or change upon operation or actuation of the manipulation element. Also sensors for detecting a position or adjustment of the manipulation element will generally be present anyway.

In this context, it is to be pointed out that an adjustment of the manipulation element from an initial position in association with an actuation of the manipulation element, does not necessarily have to be utilized immediately as a changed value of the respective ventilation parameter in the control of the ventilation operation of the patient performed by the ventilation device. In many cases it is even desirable that a change in the respective ventilation parameter in association with the adjustment of the manipulation element does not have an effect on the ventilation until the respective newly set parameter value has been confirmed. This confirmation can take place on the part of the ventilation device, for example after the ventilation device has detected that the manipulation element after adjustment has remained in a new position without further adjustment for a predetermined period of time and the ventilation device is configured such that it then considers this new position to be the desired end position. A corresponding feedback to the user that the newly set parameter value has been adopted by the ventilation device is then sensible, for example acoustically, visually or also haptically. However, for taking over or adopting a parameter value that is newly set by adjustment of the manipulation element, there will often be demanded a confirmation by the user himself, for example by the user operating the manipulation element accordingly or operating another manipulation element. For example, in the case of a manipulation element designed as a rotary/push-type actuator, a ventilation parameter can be adjusted by rotating the manipulation element from an initial position to a position corresponding to the new value, while confirmation of a newly set value requires a sub-sequent, additional depression of the manipulation element. Only after confirmation will the newly set value for the respective ventilation parameter be adopted by the ventilation device in the ventilation of the patient and be used from then on.

With such a configuration, it makes sense to generate the haptic feedback mentioned here on the basis of an adjustment of the manipulation element from an initial position (and not on the basis of a parameter value actually used for ventilation), because the adjusted parameter value has not yet been adopted by the ventilation device and the change in the respective ventilation parameter associated with the adjustment of the manipulation element does not yet take effect on the ventilation. Therefore, if in the context of the present disclosure, reference is made to a "currently set value" of a ventilation parameter, this is to be understood as a value of the respective ventilation parameter corresponding to an adjustment of the manipulation element as it would arise if the presently set value would be confirmed and adopted by the ventilation device. The haptic feedback is thus based on a simulation of the ventilation in accordance with the current adjustment of the manipulation element and possibly even reflects such a simulated ventilation situation. This applies equally to the first haptic feedback already mentioned above and to the second haptic feedback to be explained below.

In particular, the control unit can be designed to automatically determine the target value for the at least one ventilation parameter in continuous manner, in particular synchronized with respective breathing cycles. The control unit thus provides a partially or completely, in any case almost completely, automated ventilation procedure which runs in the background and which continuously, in particular synchronized with the breathing cycles, sets or adjusts all relevant ventilation parameters to suit the patient's current situation. In principle, the control unit would be able to continuously adapt all relevant ventilation parameters so that manual settings or adjustments of these ventilation parameters as such would be superfluous.

As already mentioned, it is expedient if the first haptic feedback unit is designed to control the manipulation element such that the position of the manipulation element corresponding to the target value of the at least one ventilation parameter determined by the control unit is emphasized so that it can be felt by the operator. This can take place, for example, by a feedback which gives the operator a "click" feeling or "latching" feeling when a target value determined by the control unit is reached or exceeded. For example, an abrupt change in resistance that the manipulation element opposes to a manipulation movement shortly before reaching the target value would be conceivable, in particular an abrupt decrease in this resistance. Accordingly, the resistance would then change abruptly in the opposite direction shortly after the target value was exceeded, that is to say in particular it would increase abruptly again. Other haptic feedback kinds are also conceivable, as explained in more detail below.

In a further optional development, the first haptic feedback unit can be designed to generate a first haptic feedback determined on the basis of a deviation between the value of the ventilation parameter currently set by manual operation of the manipulation element and the target value of the ventilation parameter determined by the control unit.

Such a configuration is also considered to deserve independent protection. Therefore, in a further aspect of the present invention independent of the subject matter of claim 1, a ventilation device for mechanical ventilation of patients is suggested, comprising: an operating device for setting at least one ventilation parameter, having a manipulation element that can be manually operated by an operator for manually setting the at least one ventilation parameter, and a control unit which is designed to automatically determine a target value for the at least one ventilation parameter on the basis of detected values of characteristic variables, the operating device having a first haptic feedback unit associated therewith which is designed to generate a first haptic feedback on the basis of a deviation between the value of the ventilation parameter currently set by manual operation of the manipulation element and the target value value of the ventilation parameter determined by the control unit.

As already mentioned at the beginning, the term deviation is to be understood in general to include any deviation whatsoever of the currently set value of the ventilation parameter from the target value. Such a deviation can be detected, for example, as a difference, a ratio or a different relationship between the currently set value and the target value. To implement this embodiment, a deviation can be provided in the form of a function that establishes a relationship expressing the deviation between the value of the ventilation parameter that is currently set in the course of a manipulation process at the manipulation element and the respective target value for this ventilation parameter that is currently calculated by the control unit or derived. This function can be used to generate a haptic feedback. This haptic feedback can directly reproduce the function on which it is based. Alternatively, it is also conceivable that another variable is superimposed on this function, for example an abrupt change in the haptic feedback when the target value is reached (usually when the function reaches an extreme value, in particular a minimum value) in order to generate a click feeling, as already explained in detail above.

It should be pointed out once again that the term "currently set value" of a ventilation parameter is to be understood as a value of the respective ventilation parameter that corresponds to a just effected adjustment of the manipulation element, as it would arise if the currently set value were confirmed and adopted by the ventilation device.

Further optional embodiments which apply to all aspects of the present invention shall be explained in more detail below. It goes without saying that each of these optional further embodiments alone can be added to the embodiments explained above, but that the optional further embodiments mentioned can also be combined in any form with the embodiments discussed above.

In some cases it may be expedient if the manipulation element has a tendency to assume a position of its own which corresponds to the target value of the ventilation parameter determined by the control unit. It can then be provided that the first haptic feedback unit acts on the manipulation element in such a way that the manipulation element, without manual operation, assumes—or in any case tries to assume—a position corresponding to the target value of the ventilation parameter determined by the control unit. Without operation or actuation by an operator, or if such an operation is not completed, the manipulation element then autonomously sets the value for the ventilation parameter determined by the control unit. Of course, a further desired haptic feedback—such as the click feeling discussed above—can be superimposed on such a haptic feedback. Ultimately, with such an embodiment, it would even be possible to implement a completely autonomous setting of the ventilation parameter by the control unit. It is important, however, that the operator has the option at any time to set a different value for the ventilation parameter than that specified by the control unit, by manual operation.

In this case, it can also be provided in supporting manner, but also independently of the variants discussed above, that the first haptic feedback unit acts on the manipulation element in such a way that the manipulation element returns to a position—or in any case tries to return to a position—corresponding to the target value of the ventilation parameter determined by the control unit when the manipulation element is released again upon effected manual operation thereof. Such behavior of the manipulation element need not necessarily be provided over the entire adjustment range of the manipulation element. Rather, it is sufficient when the manipulation element behaves in this way in an environment around the target value. For, the first haptic feedback then leads the operator towards the target value specified by the control unit as soon as the manipulation element reaches a specified range around the target value in the course of a manipulation process. As soon as the manipulation element is in this range, the manipulation element is centered as a result of the first haptic feedback at the target value specified by the control unit, at least as long as no manual operation takes place.

For example, the first haptic feedback can apply to the manipulation element a restoring force or a restoring moment having the characteristic of a spring deflected around a rest position, in particular a harmonic spring deflected around a point of rest. In any case, this characteristic can be provided in the aforementioned range around the target value. For example, it can be combined with a further haptic feedback. For example, it can be provided that the first haptic feedback is combined with a second haptic feedback which indicates a value of the ventilation parameter corresponding to the currently selected position of the manipulation element.

As already mentioned, the first haptic feedback unit can be designed to generate an abrupt change in the first haptic feedback in the course of a manual manipulation process of the manipulation element when a position of the manipulation element is passed over which corresponds to the target value of the ventilation parameter determined by the control unit. This is to mean that there is an abrupt change taking place in a feedback parameter that characterizes the first haptic feedback. In particular, this can be a feedback force or a feedback moment. The term abrupt is to be understood as a strong, in particular a sudden or discontinuous change in the value for the feedback parameter, for example a sudden or discontinuous change, or in any case an at least approximately sudden or discontinuous change of a feedback force or a feedback moment that has to be overcome for continuing the manual operation of the manipulation element. The feedback parameter in particular is to abruptly decrease when or shortly before the position of the manipulation element corresponding to the target value is reached and is to abruptly increase after the position corresponding to the target value is passed or exceeded, so that a latching feeling or a click feeling is perceptible (in particular tangible) when the position corresponding to the target value is passed.

In some cases—depending on the selected ventilation parameter to be set—it may be useful when the first haptic feedback is dependent on which one of several value ranges for the ventilation parameter involves the deviation of the value of the ventilation parameter currently set by manual operation of the manipulation element from that target value of the ventilation parameter determined by the control unit. In this way, it is easily possible to have several target values for the ventilation parameter that are preferred by the control unit, with the first haptic feedback relating in each case to the target value for the ventilation parameter which is associated with a respective range in which the manipulation element is currently located. When this range changes in the course of a manipulation process, the currently valid target value also changes.

In this regard, the several value ranges for the ventilation parameter can be separated from one another by respective value limits and the control unit can be designed to determine the value limits between the respective value ranges for the ventilation parameters continuously, in particular synchronized with respective breathing cycles. In this way, the respective intuitive support of an operator when one or more ventilation parameters are set can be automatically adapted to a change in the patient's condition.

For generating the first haptic feedback, in particular for determining the deviation between the value of the ventilation parameter currently set by manual operation of the manipulation element and the target value of the ventilation parameter determined by the control unit, the first haptic feedback unit may have at least one sensor associated therewith which is designed to detect the position of the manipulation element, in particular with respect to a reference position. Such a sensor for detecting the current position of the manipulation element will often be provided anyway. The control unit can then use a predetermined association of a current position of the manipulation element with a respective value of the ventilation parameter corresponding to this position in order to determine the deviation between the value of the ventilation parameter currently set by manual operation of the manipulation element and the target value of the ventilation parameter determined by the control unit, and can adjust the haptic feedback accordingly.

In order to give the operator an even better feeling with regard to the value for the ventilation parameter that is currently set or the value that is currently to be set, the previously discussed first haptic feedback can be combined with a second haptic feedback in addition which indicates the current actual state of the ventilation parameter, or in any case the current actual state of the ventilation parameter upon activation of the value currently set by manipulation of the manipulation element. To this end, the manipulation element may have a second haptic feedback unit associated therewith which acts on the manipulation element as a function of an actual state of the at least one ventilation parameter in terms of a second haptic feedback. The first and the second haptic feedback can be superimposed on one another. The first and the second haptic feedback in particular can form a common resistance with respect to a (possibly further) movement of the manipulation element. In this respect, the first and the second haptic feedback unit do not necessarily have to be completely independent components. Rather, the first and the second haptic feedback unit can have common components or be formed by the same components.

In particular, a common drive, which acts on the manipulation element, can be used to generate the first and second haptic feedback.

In particular, the second haptic feedback unit can apply to the manipulation element a second haptic feedback which indicates the actual state of the at least one ventilation parameter. Seen in total, this leads to a tactile feedback that can be felt by the operator, which corresponds to a superimposition of the first haptic feedback and second haptic feedback. The operator can thus take two items of information from the haptic feedback: firstly, how the respective ventilation parameter to be set would change with a further adjustment of the manipulation element, and secondly, which value of the ventilation parameter would be the value selected by the control unit in the current situation.

Also the second haptic feedback unit may have at least one sensor associated therewith which is designed to detect the at least one ventilation parameter. The sensor associated with the second haptic feedback unit at the same time can also deliver a signal associated with the first haptic feedback unit, from which the position of the manipulation element with respect to a predetermined reference position, in particular with respect to the position of the position of the manipulation element corresponding to the target value of the ventilation parameter determined by the control unit, can be detected.

In particular, the sensor can be provided to detect at least one of the following characteristic variables: current airway pressure at the airway entrance, current gas flow at the airway entrance, cumulative gas flow in the airway during the inspiration phase of a breathing cycle, cumulative gas flow in the airway during the expiration phase of a breathing cycle, carbon dioxide concentration in the breathing gas exhaled by the patient at the end of a breathing cycle, arterial oxygen saturation in the patient's bloodstream. In particular, the sensor can be designed such that it continuously or quasi continuously detects the respective characteristic variable, so that the currently set value of the respective desired ventilation parameter (for example, the maximum end-expiratory pressure PEEP) can then be determined from the data obtained from the sensor. However, it is also conceivable to design the sensor such that the data provided by the sensor are matched to the respectively desired ventilation parameter (for example the sensor determines the PEEP immediately at the end of a breathing cycle). Of course, a plurality of sensors can be provided for detecting a plurality of characteristic variables, with each thereof being provided for detecting one or more of the characteristic variables.

The control unit in particular can be designed to select a ventilation mode from a plurality of predetermined ventilation modes on the basis of the detected values of characteristic variables and to automatically determine the target value for the at least one ventilation parameter on the basis of the selected ventilation mode. For example, a ventilation time constant RC can be derived from the accumulated gas flow in the airway during the expiration phase of a breathing cycle, and the ventilation mode can be determined on the basis of this ventilation time constant RC. There is known a plurality of ventilation strategies or ventilation modes that are used depending on the patient's condition. There are also known ventilation systems which are adapted to switch between various ventilation modes automatically, i.e. substantially without manual intervention, depending on the characteristic data characterizing the condition of a patient. As an example, reference may be made to the ventilation system "ASV" (Adaptive Support Ventilation) or "INTEL-LIVENT-ASV" marketed by the applicant.

The at least one ventilation parameter to be set may comprise, for example, at least one of the following parameters: ventilation frequency, tidal volume, minute volume, inspiration time, positive end-expiratory pressure (PEEP), maximum airway pressure, oxygen concentration in the breathing gas supplied to the patient. It is also conceivable to combine a plurality of these parameters, in which case the several parameters to be set as a rule will be set one after the other using the system proposed herein.

The manipulation element can be designed as an adjusting device of any type, for example as a movable handle, rotary lever, rocker lever, seesaw member or the like. Input devices in the form of a keyboard, a mouse, a trackball, a touchpad, a tablet or the like are conceivable as well. The manipulation element will often be designed as a rotary member or comprise a setting element designed as a rotary member. Such a rotary member in particular can be designed as a rotary knob which can be rotated manually against the first and optionally second haptic feedback. The first and optionally second haptic feedback then provides a counter-torque corresponding to the respectively desired feedback, which must be overcome in order to (further) actuate the rotary element. Such rotary knobs are provided in many ventilation devices for manual adjustment of ventilation parameters. In such cases, one can in principle continue to use the existing hardware of the manipulation element and only has to ensure that the manipulation element is acted upon in accordance with the first haptic feedback and optionally with the second haptic feedback.

In certain embodiments, the manipulation element can be designed as a rotary/push-type actuator, so that different ventilation parameters can be set by different types of operation. In general, the manipulation element can be designed to set a plurality of ventilation parameters. This can be achieved, for example, by preselecting the respective desired ventilation parameter via a further manipulation element, e.g. a touchscreen, a keyboard, or another rotary or push-type element, with the desired value then being set for the respectively selected ventilation parameter with the aid of the manipulation element proper. In the case of rotary/push-type actuators, the preselection of one or more ventilation parameters can be carried out by corresponding adjustment of the manipulation element itself, e.g. by setting the manipulation element in a predetermined tilt position or translation position for preselection of the ventilation parameter and rotary movement of the manipulation element for setting the desired parameter value.

According to a further aspect, the present invention also relates to a method for providing a supportive interaction in setting at least one parameter of a ventilation device, wherein a manipulation element of an operating device for setting the at least one parameter is operated manually by an operator, and, on the basis of detected values of characteristic variables, a target value for the at least one parameter is determined automatically by a control unit, wherein the manipulation element, during manual operation thereof, is controlled in terms of a first haptic feedback such that a position of the manipulation element corresponding to the target value of the at least one parameter determined by the control unit is emphasized so as to be perceptible, in particular tangible, for the operator.

Alternatively, the present invention also relates to a method for providing a supportive interaction in setting at least one parameter in a ventilation device, wherein a manipulation element of an operating device for setting the at least one parameter is operated manually by an operator and, on the basis of detected values of characteristic variables, a target value for the at least one parameter is determined automatically by a control unit, wherein the manipulation element, during manual operation of the manipulation element, is acted upon with a first haptic feedback that is determined on the basis of a deviation between the value of the parameter currently set by manual operation of the manipulation element and the target value of the parameter determined by the control unit.

The methods suggested herein are not concerned with the operation of a ventilation device as such, but rather are directed to the aim that the ventilation device provides information for operators in an intuitively ascertainable manner. This provision of intuitively ascertainable information by the ventilation device takes place in automated manner and without any action on the part of the operator. In particular, no inputs on the part of the operator are required. Rather, the ventilation device is designed to automatically generate such information by means of a first and optionally second haptic feedback and without further action on the part of the operator. This applies to all of the method steps which will be explained in some more detail below.

These methods can analogously include all the features that have been described above with reference to a ventilation device, so that reference can be made to the corresponding description.

In particular, in the methods suggested here, the manipulation element can be acted upon by the first and optionally second haptic feedback unit in such a way that the manipulation element, without manual operation thereof, assumes a position—or in any case tries to assume a position—corresponding to the target value of the ventilation parameter determined by the control unit, or that the manipulation element returns to a position—or in any case tries to return to a position—corresponding to the target value of the ventilation parameter determined by the control unit when the manipulation element is released again upon effected manual operation thereof. The respective ventilation parameter is thus set fully automatically in accordance with the value suggested by the ventilation device.

The manipulation element can be acted upon by the first and optionally second haptic feedback unit with a restoring force or a restoring moment having the characteristic of a spring that is deflected around a rest position, in particular a harmonic spring deflected around a point of rest.

In particular, in the methods described, it is possible in the course of a manual manipulation process of the manipulation element, when the manipulation element passes or exceeds a position that corresponds to the target value of the ventilation parameter determined by the control unit, that an abrupt change in the first haptic feedback can be generated automatically by the first and optionally second haptic feedback unit, in particular such haptic feedback which produces a "latching" or "click feeling".

The first haptic feedback in the method can be dependent on which one of the several value ranges for the ventilation parameter involves the deviation of the value of the ventilation parameter currently set by manual operation of the manipulation element from the target value of the ventilation parameter determined by the control unit. The several value ranges for the ventilation parameters can be separated from one another by respective value limits and the control unit can be designed to determine the value limits between the respective value ranges for the ventilation parameters continuously, in particular synchronized with respective breathing cycles.

As described above, the method may provide that the manipulation element can be acted upon by the second haptic feedback unit in addition to the first haptic feedback generated by the first haptic feedback unit depending on an actual state of the at least one ventilation parameter, in terms of a second haptic feedback. The manipulation element can be acted upon by a second haptic feedback which indicates the actual state of the at least one ventilation parameter.

In a further aspect, the present invention also relates to a computer program product which contains program instructions, the execution of which on a data processing system implements a method as described herein.

Figure 2:
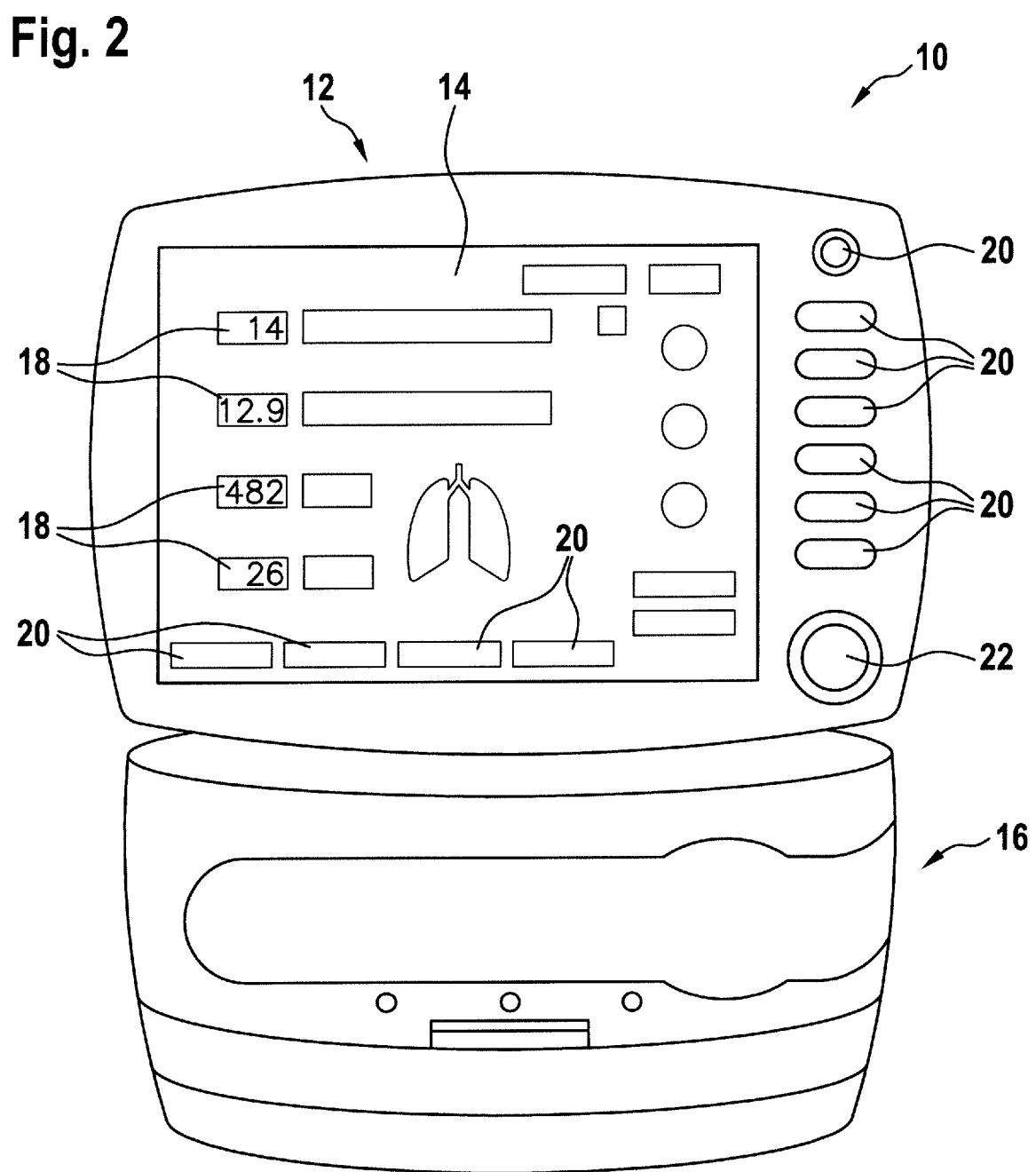
Figure 3:
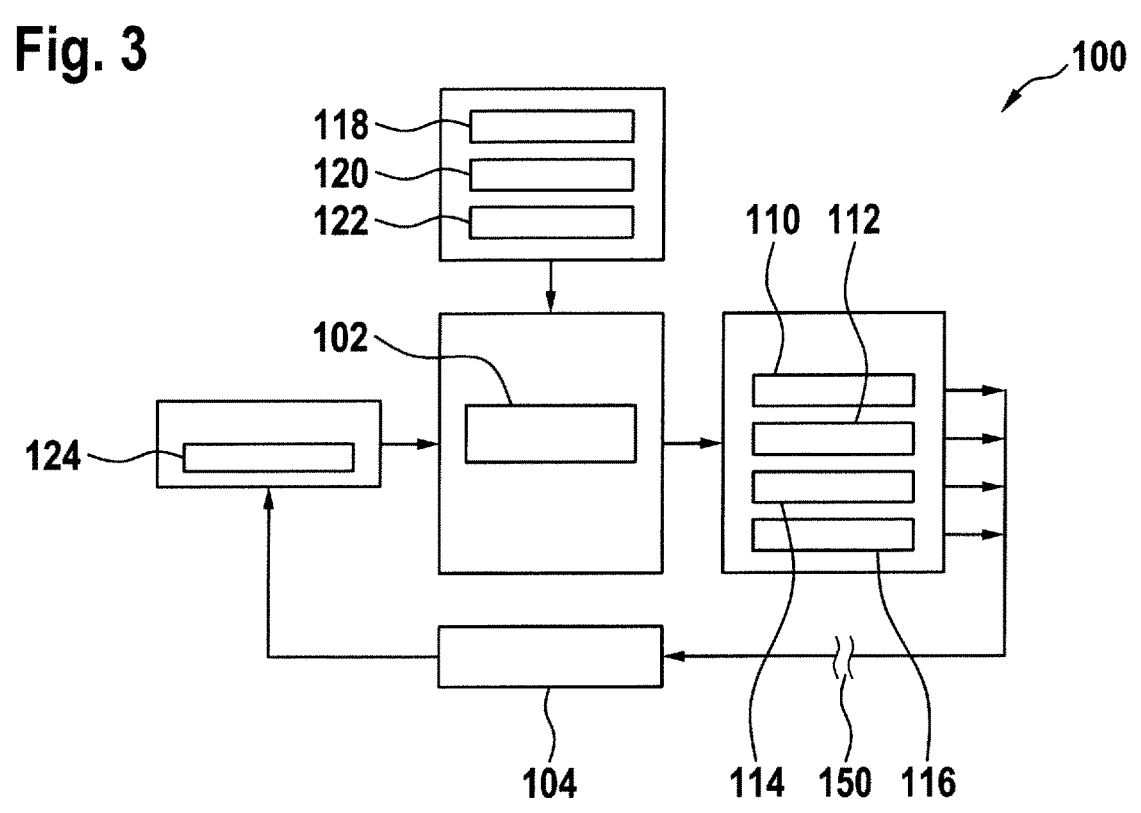
Figure 4:
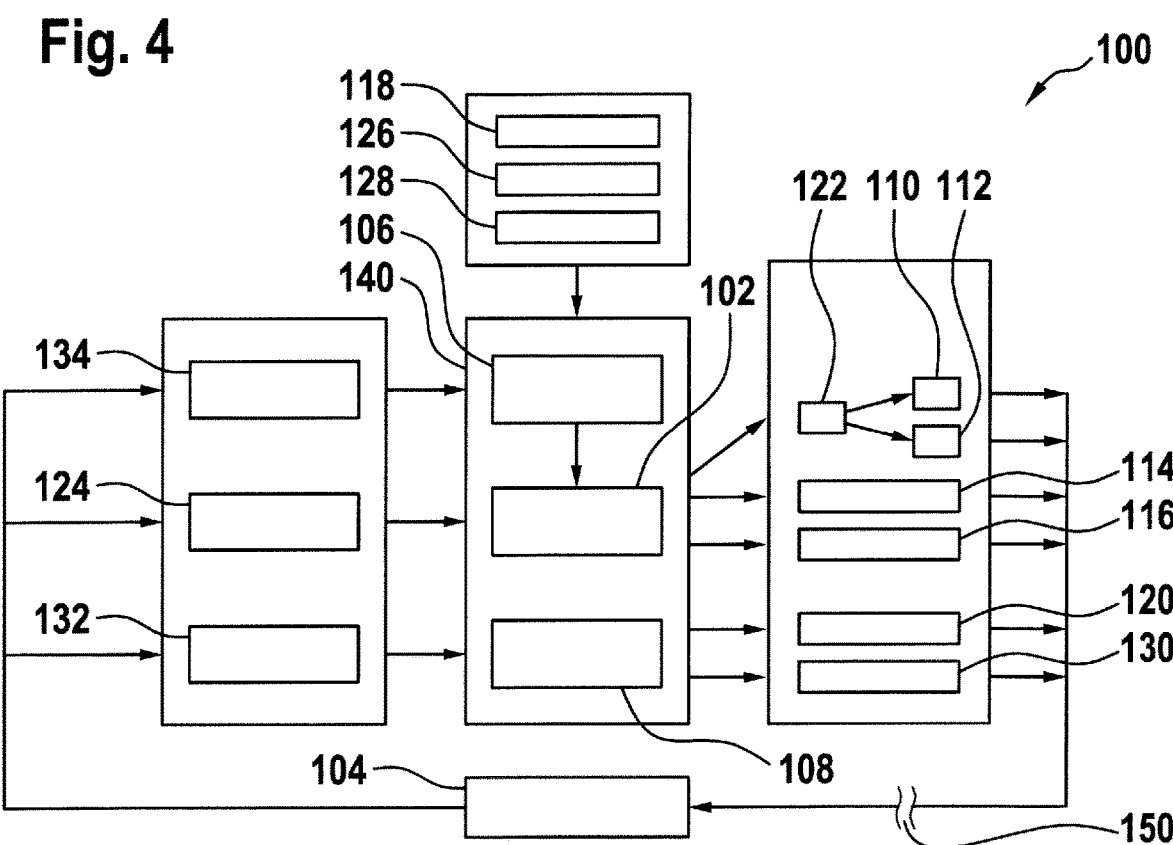
Figures 5, 6:
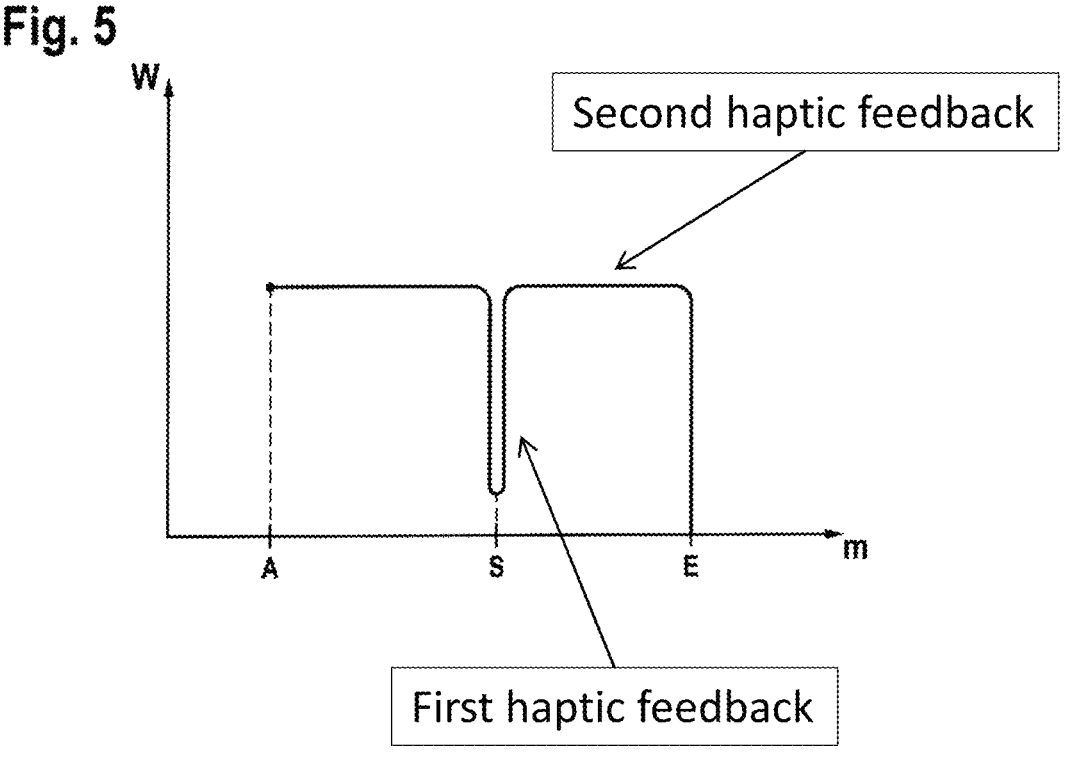

The invention will be explained in more detail below on the basis of exemplary embodiments with reference to the drawings, which show:

FIG. 1: a view of a ventilation device according to an embodiment;

FIG. 2: a view of a ventilation device according to another embodiment;

FIG. 3: a block diagram illustrating essential functional units in a control unit of a ventilation device according to FIG. 1 or FIG. 2 designed for automated determination of ventilation parameters, in accordance with a first ventilation mode "ASV";

FIG. 4: a block diagram illustrating essential functional units in a control unit of a ventilation device according to FIG. 1 or FIG. 2 designed for the automated determination of ventilation parameters, in accordance with a further ventilation mode "INTELLIVENT-ASM";

FIG. 5: a schematic view of the characteristic of a resistance with respect to an adjustment movement of a manipulation element in the course of a manual setting of a ventilation parameter according to one embodiment;

FIG. 6: a schematic view of the characteristic of a resistance with respect to an adjustment movement of a manipulation element in the course of a manual setting of a ventilation parameter according to a further embodiment.

FIG. 1 shows a view of a ventilation device 10 according to an embodiment. In particular, the ventilation device 10 comprises an operating unit 12 with a screen 14, which is arranged above a main unit 16. The main unit 16 comprises a housing in which the necessary devices for generating a breathing gas flow, in particular pumps, valves, gas supply devices and the like, are accommodated. The main unit 16 also contains a control unit, not shown in more detail (see FIGS. 3 and 4 for a schematic representation of essential functional blocks of this control unit), in which all control programs and routines required for ventilation are stored and which processes the respective control programs and routines required for mechanical ventilation. The screen 14 has a plurality of display fields, each designated 18 in FIG. 1, in which predetermined ventilation parameters are indicated. These include ventilation parameters specified for a particular ventilation mode, such as ventilation frequency, tidal volume, minute volume, inspiration time, positive end-expiratory pressure (PEEP), maximum airway pressure, oxygen concentration in the breathing gas supplied to the patient. Values for certain physiological parameters or parameters characterizing the ventilation state, which are measured by sensors, can also be shown there, such as current airway pressure at the air-way entrance, current gas flow at the airway entrance, accumulated gas flow in the airway during the inspiration phase of a breathing cycle, accumulated gas flow in the airway during the expiration phase a breathing cycle, carbon dioxide concentration in the breathing gas exhaled by the patient at the end of a breathing cycle, arterial oxygen saturation in the patient's bloodstream. In addition, there are also present graphic display fields which are not individually provided with reference numerals in FIG. 1. These graphical display fields show further information on the current ventilation procedure, for example a schematic representation of the lungs, from which information on physiological parameters, such as resistance R or compliance C, can be seen at least qualitatively, or graphical representations of the time course of certain variables which change in character over a breathing cycle, such as pulse, blood pressure, airway pressure, oxygen saturation in the blood or the like.

Moreover, the operating unit 12 has a plurality of input fields which are each designated 20 in FIG. 1. Certain commands can be input via these input fields 20, for example printouts of the functions currently displayed on the screen 14, putting the ventilation device into a standby mode, locking the screen, suppressing an alarm signal, ventilation with pure oxygen, and similar functions. The input fields 20 can be designed as mechanical, electrical or optical input devices, such as keys, knobs, buttons, switches and the like. In some embodiments, the screen 14 can be implemented as a touchscreen, so that input by the operator can be effected via the input fields 20 by touching the screen 14. It can also be provided that certain inputs can be effected by touching the screen 14 within the graphic display fields that are not designated.

In addition to the operating and display elements 18, 20 mentioned, the operating unit 12 also has a main operating or control button 22. This main operating button 22 serves for manually setting ventilation modes, as well as for manually setting ventilation parameters by an operator. The main operating button 22 thus is an example of a manipulation element which can be operated manually by an operator for the manual setting of a ventilation parameter. The main operating button 22 in the embodiment illustrated is designed as a rotary/push-type actuator. After selecting a specific ventilation parameter e.g. by touching the respective operating field 18 associated with the ventilation parameter to be selected, an operator can change a respectively set value for the ventilation parameter by turning the main operating button 22, and thus set a new desired value. After completing the setting process, the operator presses the main operating button (i.e. the operator carries out a translational actuation of the main operating button) to confirm the newly set value. After confirmation, the ventilation is continued with the newly set ventilation parameter, for example a higher or lower value for the positive end-expiratory pressure PEEP.

During the setting process, the operator can recognize the changing value of the ventilation parameter to be newly set in the respective display field 18 of the screen 14. The ventilation device 10 according to the type described here, however, allows a much more convenient and intuitive way of response of a ventilation parameter to be set, namely by means of a haptic feedback, which retroacts on the main operating button 22 in the course of a manipulation movement. In the embodiment illustrated, in which the main operating button 22 is in the form of a rotary/push-type actuator, the haptic feedback acts as a resistance or a counter-torque which is exerted by the main operating button 22 against a rotational movement forced by an operator from an initial position A in the direction towards an end position E.

It is to be noted that a corresponding haptic feedback is also exerted on the main operating button 22 when the direction of movement is reversed. When the operator reverses the direction of rotation at the main operating button 22 in the course of a manipulation process, the direction of the haptic feedback also reverses, i.e. a corresponding resistance is once again exerted in opposition to the operation of the main operating button in the reverse direction (rotation in the opposite direction).

The main operating button 22 can therefore no longer be freely rotated once a ventilation parameter has been selected, but rather only with a certain force or a certain torque which is necessary to overcome the force or the torque exerted by the haptic feedback. For generating the haptic feedback, the ventilation device 10 comprises a haptic feedback unit which is not shown in detail in the figures and which comprises, for example, a servo motor acting on an axis of rotation of the main operating button 22 as well as sensors associated therewith for detecting the current rotational position of the main operating button 22. The servo motor 22 can be controlled, for example, by the control unit 100 of the ventilation device 10, which normally receives the values obtained from the sensors of the haptic feedback unit, in addition to the values obtained from further sensors of the ventilation device 10.

The haptic feedback provided by the haptic feedback unit comprises at least a first haptic feedback (see FIG. 5) which is designed to control the main operating button 22 in terms of a first haptic feedback in such a way that a position of the main operating button 22 corresponding to the target value of the at least one ventilation parameter determined by the control unit is emphasized so as to be perceptible for the operator. Alternatively or additionally, the first haptic feedback unit can be designed to control the main operating button 22 such that the position of the main operating button 22 corresponding to the target value of the at least one ventilation parameter determined by the control unit is emphasized so as to be tangible for the operator.

In addition, the haptic feedback unit can also comprise a second haptic feedback unit which provides a second haptic feedback that acts on the main operating button 22 as a function of an actual state of the at least one ventilation parameter. The second haptic feedback thus results in a tactile signal corresponding to the adjustment of the main operating button 22 in the course of a manipulation, which allows the associated change in the to-be-set ventilation parameter to become tangible.

Seen in total, there is created a haptic feedback which corresponds to a superim-position of the first haptic feedback with the second haptic feedback, as shown in FIG. 6 and explained in more detail below with reference to FIG. 6.

FIG. 2 shows a view of a ventilation device 10 according to a further embodiment. The view according to FIG. 2 essentially corresponds to FIG. 1. The same components, or in any case components having the same function as in FIG. 1, are designated with the same reference numerals. With regard to a description, reference can be made to FIG. 1, which in this respect readily applies to FIG. 2, unless expressly stated otherwise.

FIG. 3 shows a block diagram illustrating essential functional units in a control unit 100 of a ventilation device 10 according to FIG. 1 or 2, which is designed for the automated determination of ventilation parameters, in accordance with a first ventilation mode "ASV" 102. In this ventilation mode, the control unit 100 automatically sets certain ventilation parameters such as the ventilation frequency 110, the tidal volume 112, the duration of an inspiration cycle 114 and the ventilation mode 116, while other ventilation parameters such as the minute volume (this means the product of the tidal volume and ventilation frequency) 120 or the positive end-expiratory pressure PEEP 122 can be set or specified manually. In addition, certain physiological parameters of the patient to be ventilated are also specified manually, for example, the height 118 of the same. The actual ventilation 104 is carried out on the basis of the ventilation parameters 110 to 116 determined using the ASV procedures and some of the manually specified parameters 120, 122, with certain physiological parameters still being measured during ventilation (the breathing gas flow 124 is shown in FIG. 2 as an example), which then also serve as basis for the automatic determination of the other ventilation parameters 110 to 116 by means of ASV 104.

FIG. 4 shows a further block diagram, illustrating essential functional units in a control unit 100 of a ventilation device according to FIG. 1 or 2, which is designed for the automated determination of ventilation parameters, in accordance with an even more automated ventilation mode "INTELLIVENT-ASM" 140. The ventilation mode 140 according to FIG. 4 takes place in largely automated manner and, in addition to the procedures of the ASV mode 102 already explained with reference to FIG. 3, includes furthermore procedures for controlling ventilation 106 and procedures for controlling oxygenation 108. In the ventilation mode 140, the control unit 100 sets virtually all relevant ventilation parameters in a largely automated manner, such as minute volume 120, which in turn is divided into ventilation frequency 110 and tidal volume 112, the duration of an inspiration cycle 114, the ventilation mode 116, and by means of the oxygenation procedures 106 also the PEEP 120 and the oxygen content of the ventilation gas 130. Physiological parameters such as breathing gas flow 124, $CO_2$ content of the exhaled air 134 or oxygen content in the patient's arterial blood substantially serve as the input variable for the calculation of these ventilation parameters. These parameters are fed to the routines 104, 106, 108 for the automatic determination of the other ventilation parameters 110, 112, 114 to 116, 120, 122, 130 as input variables. In addition, certain physiological parameters of the patient to be ventilated are also specified manually, for example the height 118 of the same or certain diseases 126, or certain strategies for weaning the patient from ventilation 128. This means that the ventilation in this ventilation mode takes place in completely automated manner and does not require any manual intervention on the part of an operator.

The present invention now permits ventilation procedures, such as ASV 102 or INTELLIVENT-ASV 140, which are partially or even largely automated, to be used merely as aids for assisting operators in the manual setting of ventilation parameters for mechanical ventilation. The possibility of performing the ventilation completely without manual intervention is therefore deliberately put back and instead an operator is offered support that is as easy to grasp as possible and does not interfere with the correct setting of ventilation parameters "by hand". For this reason, the values of the ventilation parameters 110-116 and 110, 112, 114 to 116, 120, 122, 130, which are determined by the automatic ventilation procedures ASV 102 and INTELLIVENT-ASV 140, respectively, are not used automatically as basis for the ventilation 104 proper, but the possibility is offered beforehand to set these ventilation parameters manually by manipulation of the main operating button 22. This is indicated in FIGS. 3 and 4 by the fact that the connection between the determined ventilation parameters 110 - 116 and 110, 112, 114 to 116, 120, 122, 130, respectively, and the ventilation 104 is interrupted in each case at the location designated 150. Thus, there is given a possibility of manually inputting ventilation parameters, in which the automatically determined values possibly can also be set quite differently. This can be expressed such that that the ventilation device indeed has fully or almost fully automated ventilation modes and also provides the same, however not for automation of the ventilation that is actually taking place, but only in the background as a support for operators in the manual setting of these ventilation parameters. This support is to be effected by haptic feedback which retroacts on a manipulation element to be actuated for manually setting the ventilation parameters.

Due to the fact that the partially or largely automatic ventilation modes running in the background continuously provide preferred values for the respective ventilation parameters to be set, this haptic feedback can take place in such a way that the respective operator receives tactile feedback when she/he sets a value for one of the ventilation parameters that matches the value set by the routine running in the background.

The haptic feedback thus comprises at least one first haptic feedback (see FIG. 5) which is designed to control the main operating button 22 in terms of a first haptic feedback such that a position of the main operating button 22 corresponding to the target value of the at least one ventilation parameter determined by the control unit is emphasized so as to be perceptible for the operator. Alternatively or additionally, the first haptic feedback unit can be designed to control the main operating button 22 such that the position of the main operating button 22 corresponding to the target value of the at least one ventilation parameter determined by the control unit is emphasized so as to be tangible for the operator.

In addition, the haptic feedback unit can also comprise a second haptic feedback unit which delivers a second haptic feedback acting on the main operating button 22 as a function of an actual state of the at least one ventilation parameter. The second haptic feedback thus results in a tactile signal corresponding to the adjustment of the main operating button 22 in the course of a manipulation, which allows the associated change in the ventilation parameter to become tangible.

Seen in total, there is thus created a haptic feedback which corresponds to a superimposition of the first haptic feedback with the second haptic feedback, as shown in FIG. 6.

FIG. 5 shows a schematic view of the characteristic of a resistance W with respect to an adjustment movement by an angle m of the main operating button 22 in the course of a manual setting of one of the ventilation parameters 110 to 116 or 110, 112, 114, 116, 120, 122, 130 according to an embodiment in which there is only a first haptic feedback. The first haptic feedback produces a tactile click feeling or latching feeling when the position of the main operating button 22 in the course of a manipulation movement for setting a new value for one of the ventilation parameters 110 to 116 or 110, 112, 114, 116, 120, 122, 130 reaches or exceeds a position S which corresponds to the value automatically determined by the routine 102 or 140 running in the background. For, if this position S is reached in the course of an adjustment movement, for example starting from an initial position A of the main 875 operating button 22 in the direction towards an end position E of the main operating button 22, a resistance W (for example in the form of a counter torque exerted by the haptic feedback unit and counteracting the adjustment movement) opposing a further adjustment movement decreases abruptly. As soon as this position S is exceeded or passed, the resistance increases again just as abruptly, which gives the operator the feeling of latching or clicking when the main operating button 22 reaches or exceeds the position S corresponding to the value automatically determined by the routine 102 or 140 running in the background.

In addition, it can also be provided that the resistance W abruptly drops to zero or almost zero when an end position E is reached which corresponds to a maximum highest permissible value or a minimum lowest required value of the parameter to be set. This gives the operator an "idle feeling" when the end position E is reached, so that the operator easily recognizes that further rotation of the main operating button 22 in the same direction will no longer bring about any further change in the set value for the ventilation parameter.

The illustration in FIG. 6 corresponds to that in FIG. 5. The illustration thus shows the characteristic of the resistance W with respect to a further movement in the same direction as a function of a displacement of the main operating button 22 by an angle m between an initial position A and a maximum permissible end position E. In addition to the first haptic feedback already explained with reference to FIG. 5, the embodiment shown in FIG. 6, upon reaching the target position S, involves furthermore a second haptic feedback which is superimposed on the first haptic feedback in addition. The second haptic feedback indicates a change in the ventilation parameter to be set with a further increase in the adjustment of the main operating button 22, for example an increase in the positive end-expiratory pressure PEEP with increasing adjustment m of the main operating button 22. In this way, the operator already receives a tactile feedback in the course of an adjustment of the main operating button 22, as to how the currently selected ventilation parameter will change when the new setting has become effective. In particular experienced operators are capable of making a good estimate of a suitable value for the parameter already on the basis of such tactile feedback. One advantage is that the procedure suggested here enables the operator to compare the value felt or estimated by him for the ventilation parameter with the value suggested by the automated procedure 102 or 140. Moreover, it is also possible to initially set the new value merely by turning the main operating button 22 to the desired position and to let this value, only after completed setting thereof, become effective in ventilation (e.g. by pressing the main operating button 22). It is thus possible to readjust again if, for example, there is a large discrepancy between the ideal value of the ventilation parameter sensed by the operator and the value suggested by the automated routine 102 or 140.

The embodiment according to FIG. 6 is designed such that the resistance W increases abruptly to a very high value when an end position E is reached which corresponds to a maximum highest permissible value or a minimum lowest required value of the parameter to be set. This gives the operator the feeling of a stop or an end limitation with respect to which the main operating button 22 cannot be rotated further. It is thus also possible to achieve the effect that the operator cannot turn the main operating button 22 beyond an end position E. Of course, the variant shown in FIG. 5, when the end position E is reached, can be used in the embodiment according to FIG. 6, if desired. Conversely, it is of course also possible to use the variant shown in FIG. 6, when the end position E is reached, in the embodiment according to FIG. 5, if desired.

The invention claimed is:

1. A ventilation device for mechanical ventilation of a patient, the ventilation device comprising:

an operating device for setting at least one ventilation parameter, the operating device having a manipulation element and a haptic feedback unit, wherein the manipulation element is manually operable by an operator to set the at least one ventilation parameter; and a control unit, including a memory and a processor, configured to receive detected values of characteristic variables and based thereon to execute a software routine stored in said memory to automatically determine a target value for the at least one ventilation parameter, wherein the haptic feedback unit is operable to control the manipulation element by application of a haptic feedback such that a position of the manipulation element corresponding to the target value of the at least one ventilation parameter determined by the control unit is emphasized so as to be perceptible for the operator, wherein the haptic feedback unit is configured to generate an abrupt change in the haptic feedback applied to the manipulation element in the course of a manual manipulation process of the manipulation element when the manipulation element passes a position that corresponds to the target value of the ventilation parameter determined by the control unit.

2. The ventilation device of claim 1, wherein the control unit is operable to automatically determine the target value for the at least one ventilation parameter in a continuous manner, in synchronization with respective breathing cycles of the patient.

3. The ventilation device of claim 1, wherein the haptic feedback unit is operable to control the manipulation element such that the position of the manipulation element corresponding to the target value of the at least one ventilation parameter determined by the control unit is emphasized so as to be tangible for the operator.

4. The ventilation device of claim 1, wherein the haptic feedback unit is configured to perform at least one of the following actions:

act on the manipulation element in such a way that the manipulation element, without manual operation thereof, assumes, or attempts to assume, a position corresponding to the target value of the ventilation parameter determined by the control unit;

act on the manipulation element in such a way that the manipulation element returns, or attempts to return, to a position corresponding to the target value of the ventilation parameter determined by the control unit when the manipulation element is released again upon effected manual operation thereof; and apply to the manipulation element a restoring force or a restoring moment having the characteristic of a spring that is deflected around a rest position.

5. The ventilation device of claim 1, wherein the haptic feedback is dependent on one of a plurality of value ranges for the ventilation parameter that involves the deviation of the value of the ventilation parameter currently set by manual operation of the manipulation element from the target value of the ventilation parameter determined by the control unit.

6. The ventilation device of claim 1, wherein the haptic feedback unit further comprises at least one of the following:

a sensor operable to detect the position of the manipulation element, with respect to a reference position; and a sensor operable to detect an actual state of the at least one ventilation parameter.

7. A ventilation device for mechanical ventilation of a patient, the ventilation device comprising:

an operating device having a manipulation element and a haptic feedback unit, wherein the manipulation element is manually operable by an operator to set the at least one ventilation parameter; and a control unit, including a memory and a processor, configured to receive detected value of characteristic variables and based thereon to execute a software routine stored in said memory to automatically determine a target value for the at least one ventilation parameter, wherein the haptic feedback unit is configured to generate a haptic feedback that is determined on the basis of a deviation between the current value of the ventilation parameter corresponding to the current position of the manipulation element in the course of manual operation of the manipulation element and a target value of the ventilation parameter determined by the control unit.

8. The ventilation device of claim 7, wherein the haptic feedback unit acts on the manipulation element in such a way that the manipulation element, without manual operation thereof, assumes, or attempts to assume, a position corresponding to the target value of the ventilation parameter determined by the control unit.

9. The ventilation device of claim 8, further comprising at least one sensor for detecting at least one of the following characteristic variables:

current airway pressure at the airway entrance, current gas flow at the airway entrance, accumulated gas flow in the airway during the inspiration phase of a breathing cycle, accumulated gas flow in the airway during the expiration phase of a breathing cycle, carbon dioxide concentration in the breathing gas exhaled by the patient at the end of a breathing cycle, and arterial oxygen saturation in the patient's bloodstream.

10. The ventilation device of claim 7, wherein the haptic feedback unit acts on the manipulation element in such a way that the manipulation element returns, or attempts to return, to a position corresponding to the target value of the ventilation parameter determined by the control unit when the manipulation element is released again upon effected manual operation thereof, and wherein the haptic feedback applies to the manipulation element a restoring force or a restoring moment having the characteristic of a spring that is deflected around a rest position.

11. The ventilation device of claim 7, wherein the haptic feedback unit is operable to generate an abrupt change in the haptic feedback in the course of a manual manipulation process of the manipulation element when the manipulation element passes a position that corresponds to the target value of the ventilation parameter determined by the control unit.

12. The ventilation device of claim 7, wherein the haptic feedback is dependent on one of a plurality of value ranges for the ventilation parameter that involves the deviation of the value of the ventilation parameter currently set by manual operation of the manipulation element from the target value of the ventilation parameter determined by the control unit, and wherein the plurality of value ranges for the ventilation parameter are separated from one another by respective value limits, and the control unit is designed to determine the value limits between the respective value ranges for the ventilation parameter continuously, in synchronization with respective breathing cycles of the patient.

13. The ventilation device of claim 7:

wherein the haptic feedback unit comprises at least one of the following: a sensor operable to detect the position of the manipulation element, with respect to a reference position; and a sensor operable to detect an actual state of the at least one ventilation parameter.

14. The ventilation device of claim 13, wherein at least one of the following is true:

the haptic feedback unit applies to the manipulation element a second haptic feedback which indicates the actual state of the at least one ventilation parameter; and the haptic feedback unit has at least one sensor associated therewith which is operable to detect the at least one ventilation parameter.

15. The ventilation device of claim 7, wherein at least one of the following is true:

the control unit is operable to select a ventilation mode from a plurality of predetermined ventilation modes on the basis of the detected values of characteristic variables and to automatically determine the target value for the at least one ventilation parameter on the basis of the ventilation mode selected;

the at least one ventilation parameter comprises at least one of the following parameters: ventilation frequency, tidal volume, minute volume, inspiration time, positive end-expiratory pressure (PEEP), maximum airway pressure, oxygen concentration in the breathing gas supplied to the patient; and the manipulation element is designed as a rotary member or comprises an adjusting element formed as a rotary member.

* * * * *